United States Patent [19]

Wylie et al.

[11] Patent Number: 4,981,802

[45] Date of Patent: Jan. 1, 1991

[54] METHOD AND APPARATUS FOR STREAKING A CULTURE MEDIUM

[75] Inventors: Colin Wylie, Edmonton; Aimo Pitkanen, Fauquier, both of Canada

[73] Assignee: Vista Laboratories Ltd., Edmonton, Canada

[21] Appl. No.: 32,235

[22] Filed: Mar. 31, 1987

[30] Foreign Application Priority Data

Apr. 18, 1986 [CA] Canada .................................. 507018

[51] Int. Cl.⁵ .............................................. C12M 1/26
[52] U.S. Cl. .................................... 435/294; 435/292; 435/293; 435/295; 435/297; 435/298; 435/30
[58] Field of Search .......................... 435/30, 292–295, 435/297, 298

[56] References Cited

U.S. PATENT DOCUMENTS

| | | |
|---|---|---|
| 3,623,958 | 11/1971 | Fitzgerald . |
| 3,935,075 | 1/1976 | Perry et al. . |
| 4,010,077 | 3/1977 | Pardos .............................. 435/294 |
| 4,144,135 | 3/1979 | Sequeira ............................ 435/293 |
| 4,287,301 | 9/1981 | Astle . |

*Primary Examiner*—Robert J. Warden
*Assistant Examiner*—Timothy M. McMahon
*Attorney, Agent, or Firm*—Cushman, Darby & Cushman

[57] ABSTRACT

This invention relates to an apparatus and method for streaking a sample on a Petri plate. The objective is to provide a method and apparatus in which the inoculum is sequentially streaked in a series of dilutions in a manner closely simulating previous manual practice but with a consistency, safety and accuracy which is not manually achieved. A sequential series of spreader heads are brought into contact with the culture medium on a Petri plate and swept back and forth over the medium surface to streak the inoculated sample in a segment of the plate. The paths of the second and subsequent spreading heads are angularly displaced from the path of the preceding spreading head, so that the segment of the plate in which the second and subsequent spreading heads streak the sample will partially overlap the respective preceding segment. This is best achieved by oscillating the support of the Petri plate and sequentially moving a spreading head radially during such oscillation. Provision is included for sterilizing the spreading head. Provision is also included for successively processing a series of Petri plates.

26 Claims, 21 Drawing Sheets

METHOD AND APPARATUS FOR STREAKING A CULTURE MEDIUM

This invention relates to an apparatus and method for streaking a specimen over a culture medium surface to assist in the isolation and identification of the specimen.

The isolation and identification of a sample or specimen has for many years involved the streaking of the sample onto a culture medium. The specimen is streaked in such a manner as to provide an increasing dilution of the sample. It will then grow in the nutrient medium. The streaked culture medium plates are incubated and then examined or subjected to tests to isolate and identify the bacteria or other microorganisms in the sample. This streaking procedure is time consuming, inconsistent and biohazardous. It is also difficult to maintain consistency between the techniques used by different technicians or even between different samples prepared by the same technician at different times.

The usual procedure is to deposit the unknown sample on the culture medium which is contained in a Petri plate. Then a sterile spreading wire will be used to streak the sample over the surface of the culture medium. A new sterile wire loop is then used to streak part of the sample in a further area of the Petri plate so as to achieve a lower concentration. This procedure may be repeated a third and a fourth time so as to obtain streaks at four different concentrations. It will be appreciated that the technician must be skilled and even then it is difficult to achieve consistent and accurate results. Furthermore, this procedure is extremely time consuming and potentially biohazardous. An alternative method is to use a glass spreader in a fashion similar to a wire loop or to spread the sample in non-overlapping sequential streaks of diminishing concentration.

There have been attempts to provide automatic streaking. For example, U.S. Patent issued Nov. 30, 1971 to James E. Fitzgerald, and U.S. Pat. No. 4,287,301 which issued Sept. 1, 1981 to Thomas W. Astle, describe methods and apparatus intended to provide automatic streaking. However, the apparatus described in these patents does not adequately reproduce the effect of manual streaking, particularly where it is desired to streak at several different concentrations using a sterile spreading head for each concentration. These prior devices are inconvenient to use and do not provide a practical solution to the provision of properly streaked plates.

The object of this invention is therefore to provide a method and apparatus for streaking a sample on a Petri plate which closely simulates the effect of established manual procedures, but with improved consistency, accuracy and safety, and which is capable of streaking at several concentrations.

The preferred embodiment of this invention has as its further object to provide an overall spreading, transport, storage and handling system which integrates and improves standard procedures and techniques.

In accordance with a broad aspect of this invention, apparatus is provided for streaking a sample on a Petri plate having a layer of culture medium inoculated with a sample comprising means for contacting a first spreading head with the culture medium, means for sweeping said spreading head back and forth across the surface of the culture medium, preferably in a sinuous path in a first segment of the plate and means for contacting a second spreading head with the culture medium and means for sweeping said second spreading head back and forth across the surface of the culture medium in a second segment of the plate angularly displaced but overlapping the segment in which the preceding spreading head has streaked the sample.

In accordance with a further preferred aspect of this invention, the Petri plate is mounted on a support for oscillation about a vertical axis. The spreading heads are sequentially brought in contact with the surface of the culture medium and moved radially from close to the periphery of the Petri plate towards the center while the plate is subjected to a plurality of oscillations to streak the inoculated sample. The second spreading head is arranged to streak the inoculated sample in a segment of the culture medium overlapping the segment streaked by the first spreading head. Similarly, if there are third and fourth spreading heads, these will streak segments which partially overlap the preceding segment.

In accordance with another aspect of this invention, the spreading head comprises a wire element, means are provided for automatically heating the wire element to sterilize it when the element is not in contact with the sample.

In accordance with yet a further aspect of the invention, the spreading heads are carried by spreader arms extending in directions lateral to the support for the Petri plate. A cam actuates each of the spreader arms to advance or retract it in a radial direction. Another cam actuates each spreader arm to raise or lower the spreader head onto the culture medium and remove it therefrom.

A further aspect of this invention includes means for stacking a number of Petri plates, means for moving successive Petri plates to an orientation position where the Petri plate will be rotated to align the place where the Petri plate was inoculated in a predetermined position. Means are also provided for moving the Petri plate from the orientation position to a work position where the spreading heads are successively brought in contact with and moved across the surface of the culture medium. Means may also be provided for separating the covers from each Petri plate and for moving the Petri plates and associated but separated covers from the orientation position to the work position.

Another aspect involves a carousel as the means for stacking referred to in the previous paragraph. The carousel is removable so as to function as a transport and storage vehicle in addition to its contribution to the operation of the apparatus.

Further aspects of this invention will be apparent from the detailed description.

In the drawings which illustrate this invention;

Figure 1:
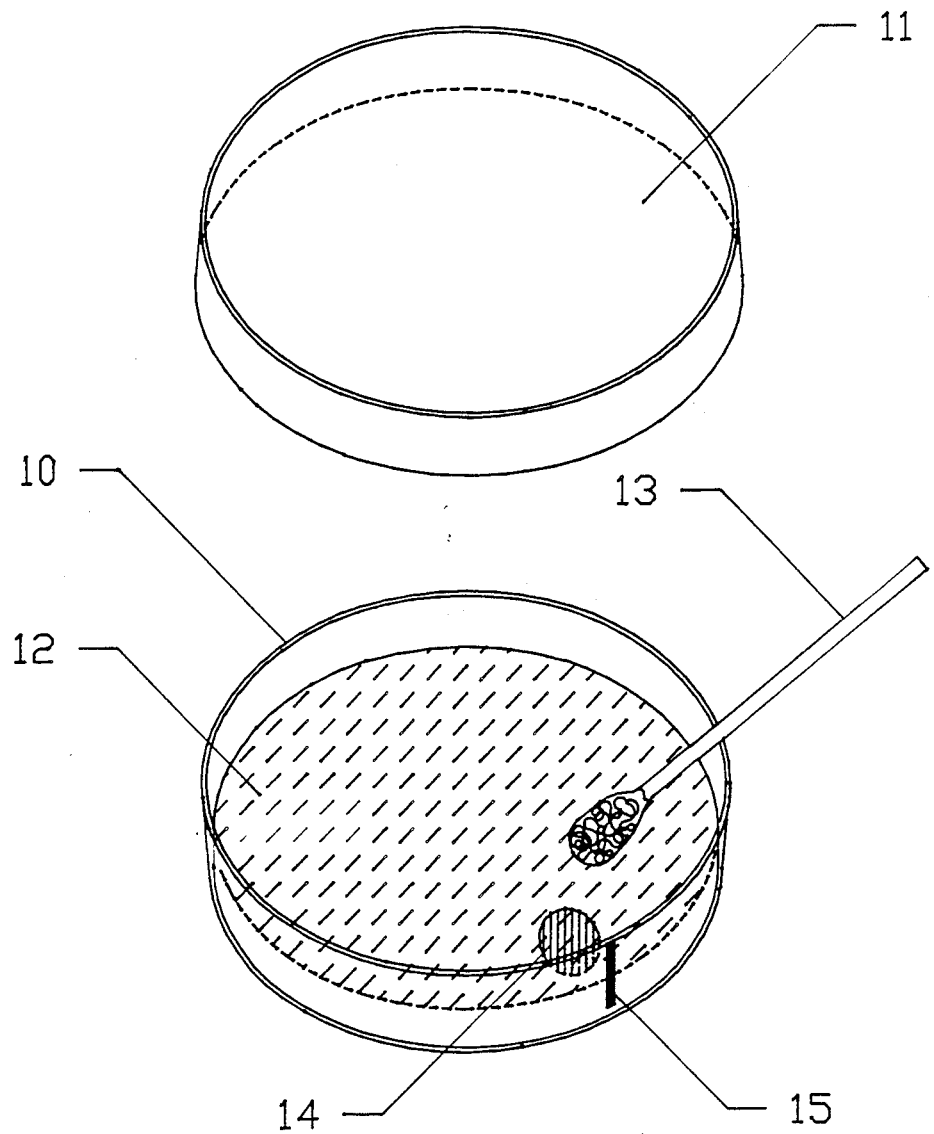
FIG. 1 is a isometric view of a Petri plate and cover.

Referring generally to the drawings, FIG. 1 illustrates a Petri plate 10 having a lid 11 and containing a layer of culture medium 12. The laboratory technician inoculates the Petri plate with an unknown sample 13 for microbiological analysis such as a clinical specimen, (e.g. throat swab or urine sample) a food sample or a pharmacological sample. The sample is inoculated at 14 in line with an orientation mark 15 or alternatively, after inoculation orientation mark 15 may be affixed with a wax stencil or the like. The lid is then replaced and the Petri plate is ready to be processed in accordance with the apparatus of this invention.

Figure 2:
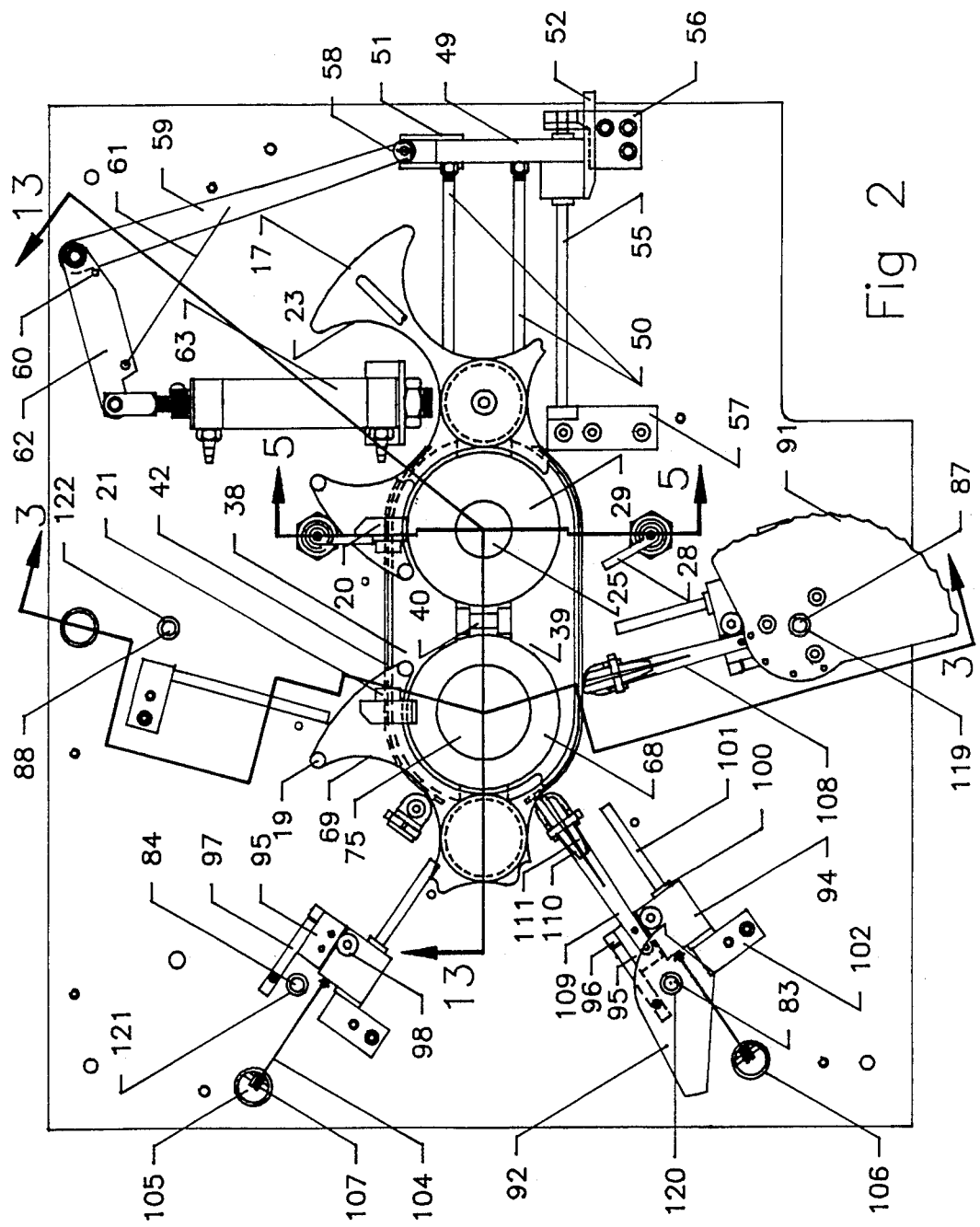
FIG. 2 is a top plan view of an apparatus in accordance with this invention which has been partially cut away to show details of the apparatus.
Figure 3:
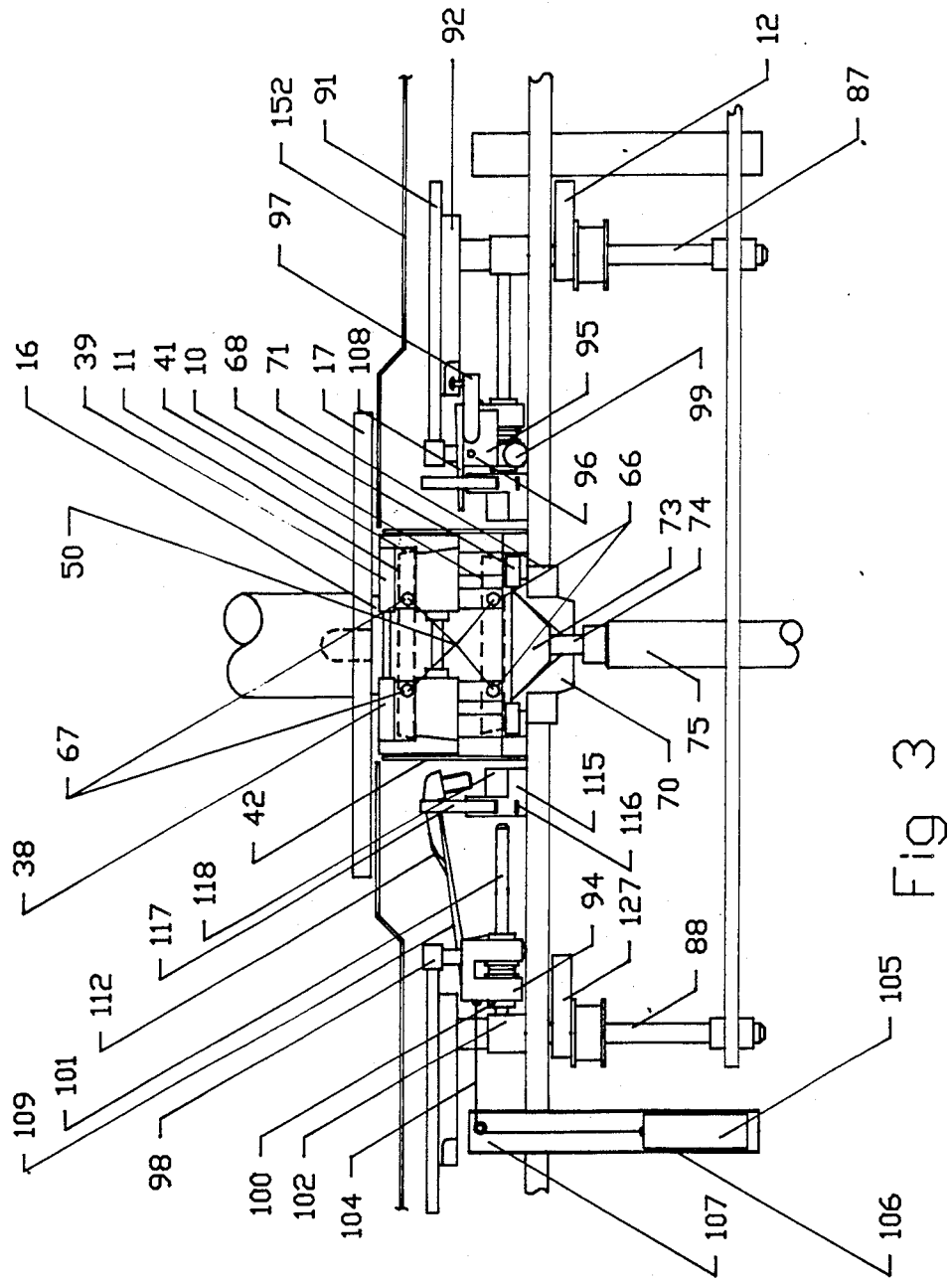
FIG. 3 is a section view on the line 3—3 of FIG. 1.

The apparatus of this invention is illustrated in top view in FIG. 2. FIG. 3 is a sectional view along the line 3—3 of FIG. 2.

Figure 4:
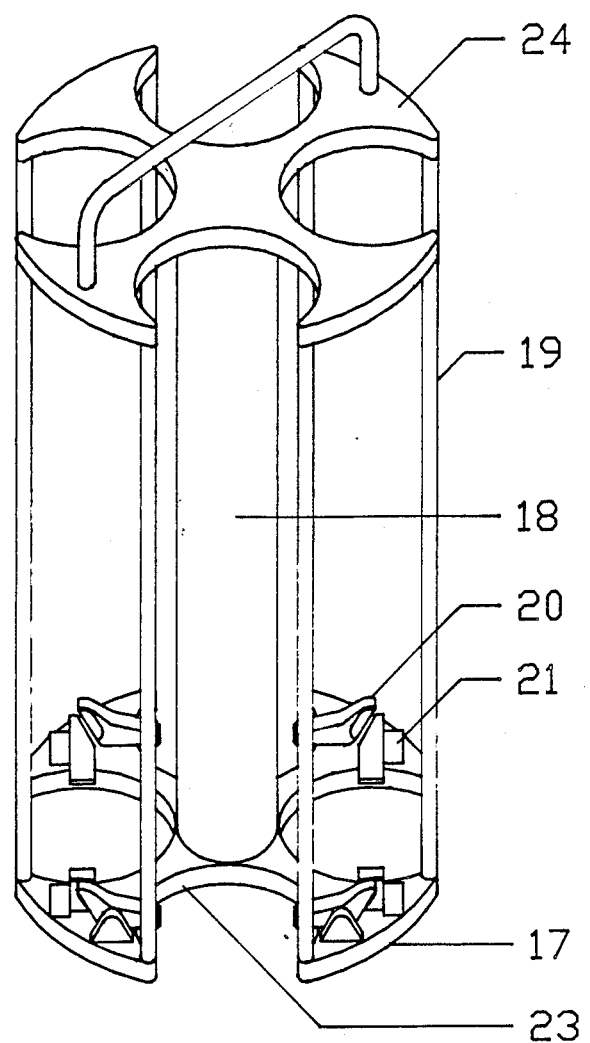
FIG. 4 is a isometric view illustrating a carousel for use in the apparatus of this invention.

The apparatus illustrated in FIGS. 2 and 3 includes a carousel 17 mounted on a carousel support 16 and containing vertically extending slots or guides 18 for the reception of inoculated Petri plates with their lids. Carousel 17 is shown in detail in FIG. 4 from which it will be noted that slots 18 extend from top to bottom of the carousel to permit the technician to load the Petri plates at the top and to permit the plates to be unloaded at the bottom. The Petri plates are prevented from descending from the carousel prematurely by a petri plate stack support 20 which is shown in detail in FIG. 5 and includes a spring 22 which tends to bias the stack support 18 in an extending direction, with respect to FIG. 5 allowing the plates to be loaded into the carousel from beneath when desired. The carousel may, for example, hold about eighty plates in total of four stacks of twenty plates each. The carousel as shown in FIG. 4 includes a bottom or frame 23 and a top or frame 24 connected by rods 19. Load actuators 28 are positioned so that they rotate about a vertical axis and move vertically and pivot stack support 20 to enable the carousel to be unloaded downwardly. Load actuators 28 can then be used to flip the Petri plate retainers back into the position shown in FIG. 2.

Figure 6:
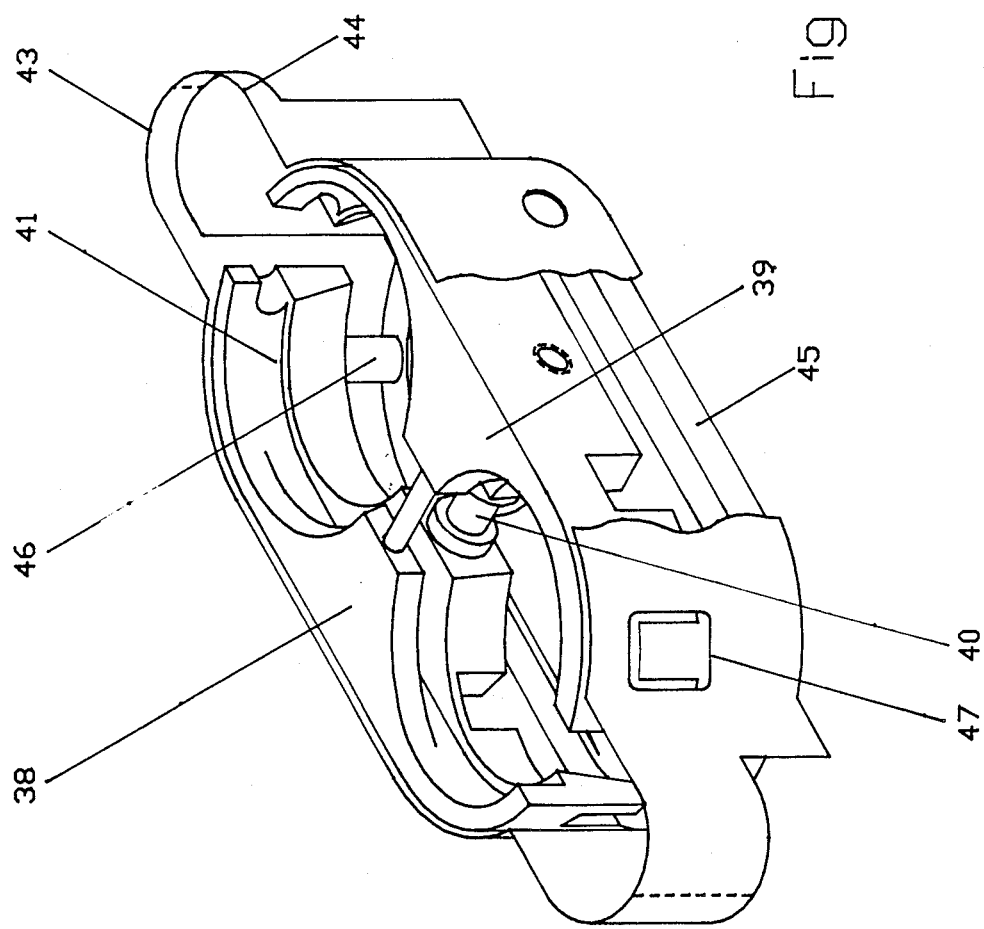
FIG. 6 is an isometric view of a plate guide.

The initial stack of Petri plates in carousel 17 is lifted by load cylinder 27 which is in the centre of orientation station 29 and load actuators 28 pivot stack support 20 out of the way so that individual plates can be sequentially down-loaded on to the orientation station. During this down-loading on to the orientation station, the Petri plate lid is removed by a plate guide 37 which is shown in detail in FIG. 6 and which traps Petri plate lid 11 while permitting the Petri plate 10 to descend. Plate guide 37 is in two sections 38 and 39 which can be adjustably spaced by screw 40 to accommodate different diameters of Petri plates and lids. The slots in the ends of sections 38 and 39 allows space for transfer arms 50. Lip 41 which holds the lid extends horizontally along plate guide 37 as shown in FIG. 6. Shroud 42 supports plate guide 37. Plate guide 37 also includes apertures 47 for the passage of spreading heads as will subsequently be described. In the orientation station 29, the Petri plate is caused to rotate until the orientation mark 15 is located by a sensor 221. If a grease pencil has been used this can be detected using infrared fibre optics. When the load cylinder 27 reaches the bottom of its stroke a switch 226 energizes the orientation motor 275 shown in FIG. 12 and energizes sensor 221.

Figure 7:
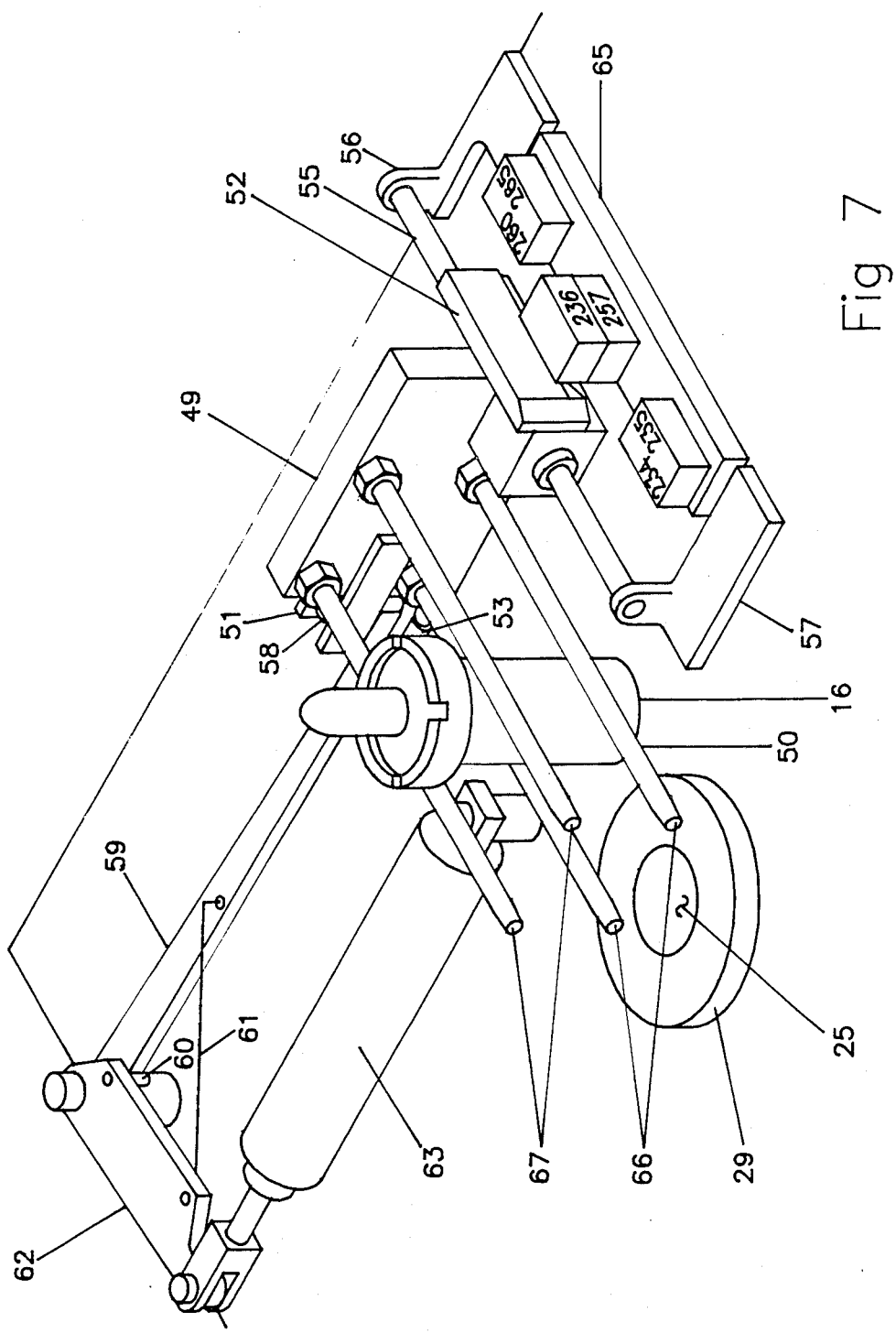
FIG. 7 is a detail isometric view of a transfer carriage.

A transfer carriage 48 is provided with four transfer arms 50 two of which bear on the Petri plate as shown at 66 and two of which bear on the lid as shown at 67. These travel between plate guides 37 until work station 68 is reached. The transfer carriage which is shown in detail in FIG. 7, is advanced and retarded by transfer cylinder 63 through transfer actuator ASS-58 to 62. Actuator arm 59 has at its end cam roller 58 which slides between brackets 51. It follows along guide rod assembly 54 and rides on cam roller 53. Switch actuator or striker 52 actuates switches on switch assembly 64. Switch 260 signals that the carriage is fully retracted, so that down-loading can proceed. Switch 257 allows the load piston 25 to extend and support the next plate. Switch 235 starts up the main motor and 234 initiates transfer slide retraction. Switch 236 overrides switch 235.

Figure 8:
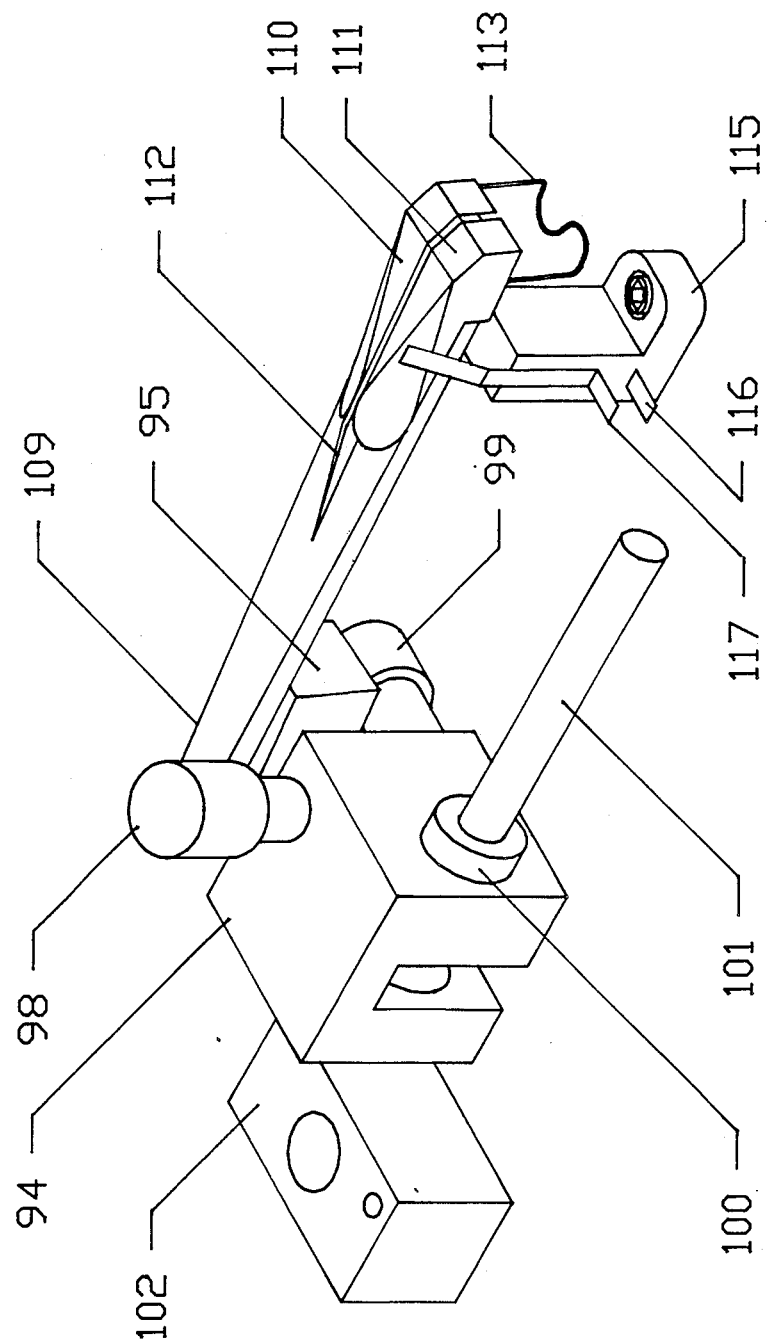
FIG. 8 is a detail isometric view of a spreader head and its electrical contacts.
Figure 9:
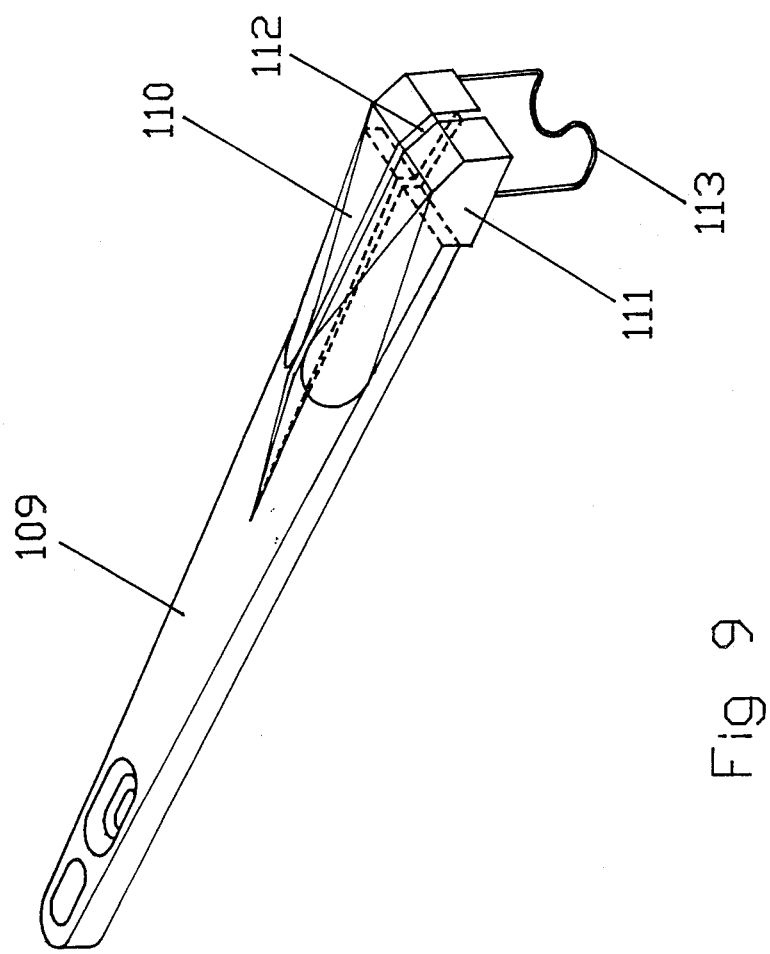
FIG. 9 is a detail isometric view of the spreader head shown in FIG. 8.
Figure 10:
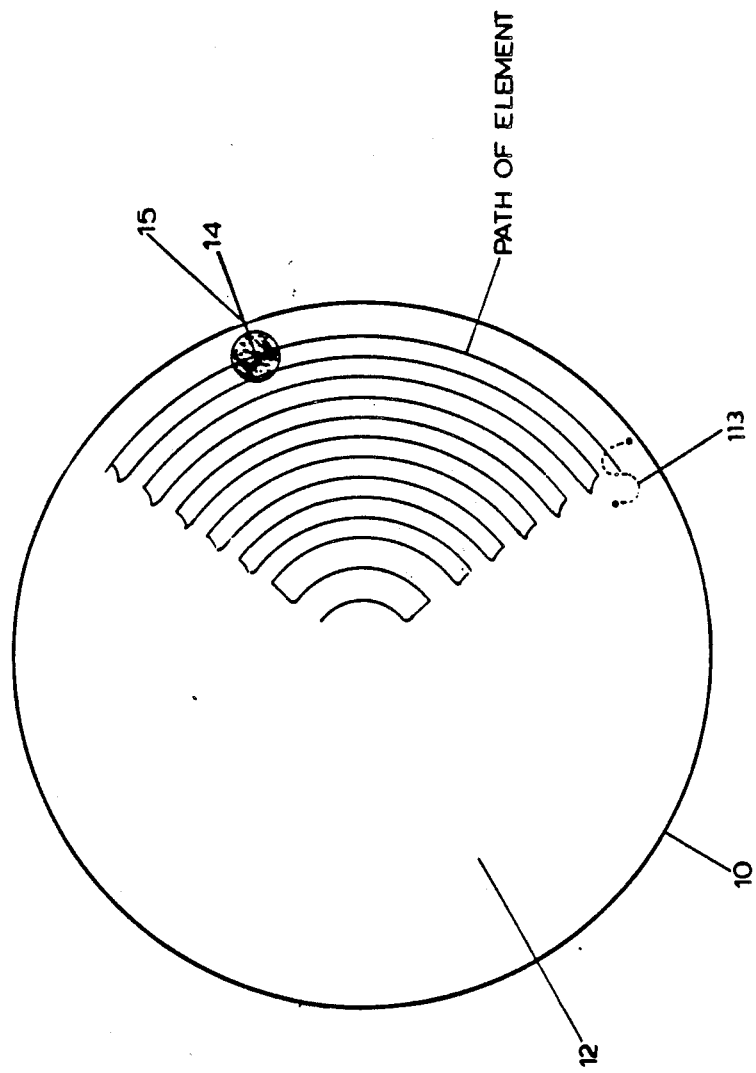
FIG. 10 is a plan view of a Petri plate showing in detail the path followed by the spreader element.
Figure 12:
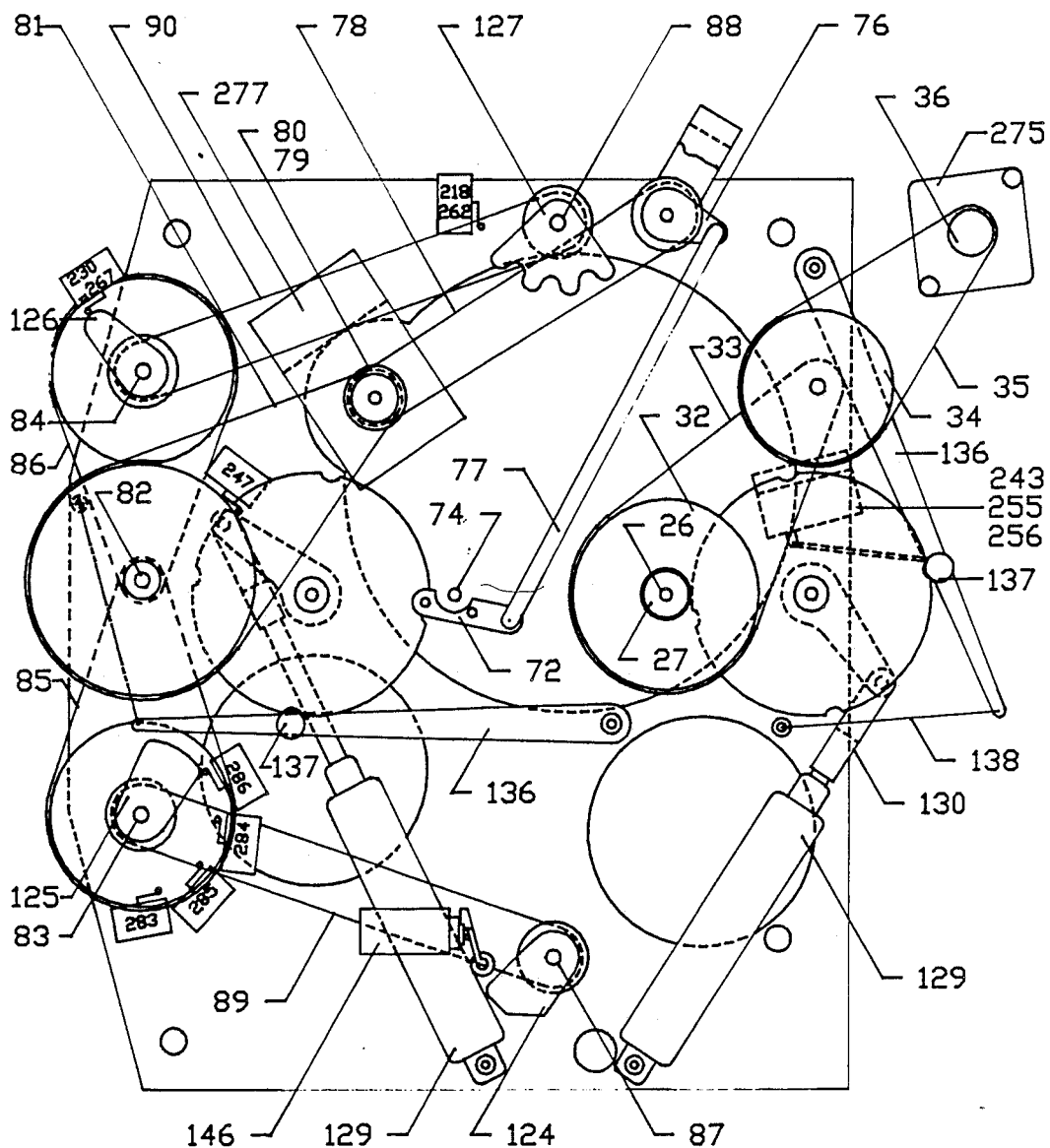
FIG. 12 is a top view with top plate removed to show the driving mechanism.

In the work station the Petri plate is supported on an oscillating disc 68 within which there is an unload cylinder 75. Disc 68 oscillates through an angle of about 110°. A spreading head in the form of a wire element 113 which is shown in detail in FIGS. 8 and 9, is caused to descend onto the nutrient medium and to be moved across its surface from the periphery to the centre of the plate. This movement is radial. During such movement disc 68 is oscillated. The combined effect therefore, of the oscillation and this radial movement will be that the spreading element 113 follows a path of concentric arcs joined by radial segments at the ends of the arcs as illustrated in FIG. 10 to streak the sample 14. Element 113 is mounted on a spreader arm 109, which is preferably removable. The leading portion of head 108 is in the form of L-shaped copper bars 110 and 111 separated by a layer of insulation 112 so that the only electrical connection is through element 113. Electrical contacts 116 and 117 make contact with L-shaped copper bars 110 and 111 when head 108 is fully retracted. Electrical contacts 116 and 117 are mounted on support block 115 which contains a well 118 to collect ash or incinerated debris from element sterilization. When head 108 is in its retracted position and electric contacts 116 and 117 are in contact with bars 110 and 111 a low voltage AC current which is controlled by sterilization cam 125 shown in FIG. 12, heats element 113 to incandescence, effectively sterilizing it for use on the next plate. The spreader head 108 is controlled by a carriage 94 which is controlled by an arrangement of cams. The components are illustrated in partly cut away form in FIG. 2 in relation to the four spreader units generally indicated at 119, 120, 121 and 122 which are of identical construction except for the timing of the operation and their location. The spreader unit includes a support block 102 to which is connected a guide rod 101 on which a carriage 94 moves. Carriage 94 has a cam follower 98 the position of which is controlled by cam 91. Cam 91 is mounted on vertical shafts 83, 84, 87 and 88. Rotation of cam 91 causes carriage 94 to advance in a predetermined manner during the treatment of each Petri plate. Retraction and tension are achieved by counterweight 105 which moves in guide tube 106 and tension line 104 passing over pulley 107 and being connected to carriage 94. Cam shafts 83, 84, 87 and 88 are also provided with a lift cam 92 which acts on lift cam follower 97 to lift the spreader head 108 into raised position thus enabling the spreader element 113 to be lowered onto the culture medium. Spreader head 108 is weighted to provide appropriate pressure of element 113 on the surface of the medium 12. The operations of drive cam 91 and lift cam 92 are coordinated so that wire spreading element 113 of unit 108 is lowered onto the surface of the culture medium 12 in the Petri plate 10, and is then moved along the surface of the culture medium 12 radially towards the centre while the plate is oscillating through 110° cycles. Spreading head 108 is then withdrawn, making electrical contact with contacts 116 and 117. Sterilization cam 125 in FIG. 12 will then energize the circuit to heat element 113 to incandescence sterilizing it so that it will be ready for treatment of the next Petri plate. Current sensor cam 127 in FIG. 12 provides a safety feature verifying element integrity by monitoring current flow to close down the operation of the system if there has been a failure to sterilize a spreading element.

Spreader assemblies 120, 121 and 122 are angularly spaced from spreader assembly 119 so that the spreading elements associated with them will act on different segments of the culture medium in succession.

Figure 11:
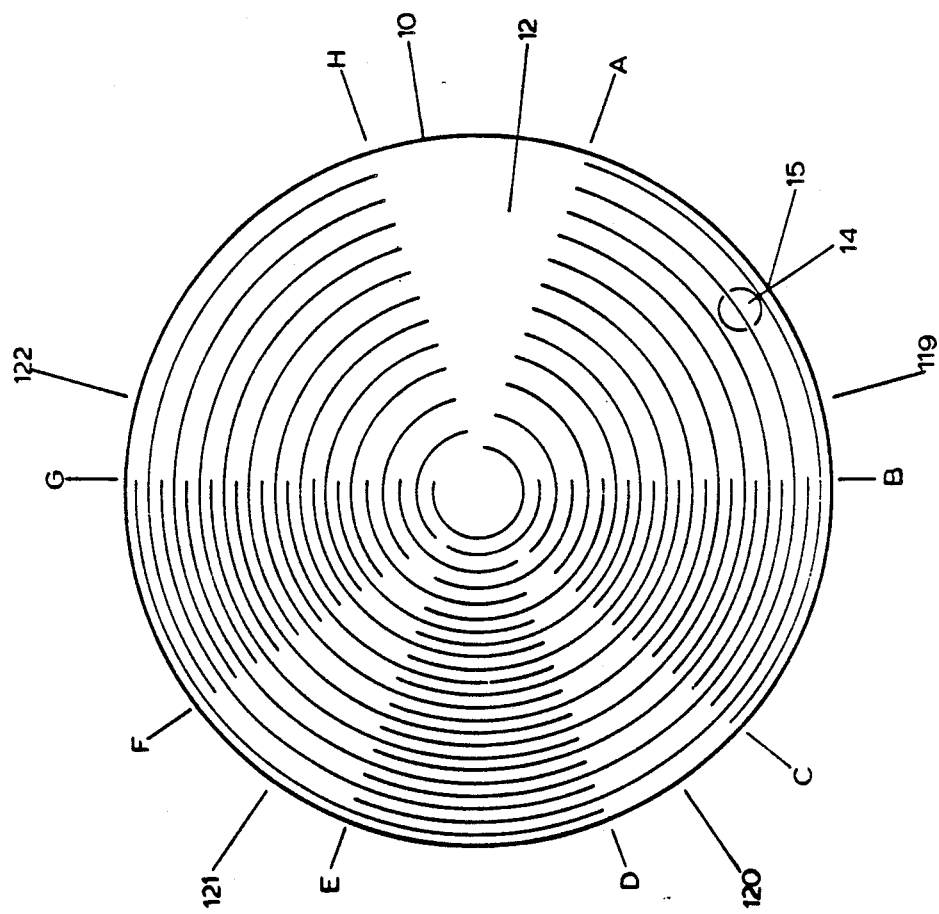
FIG. 11 is a plan view of a Petri plate illustrating the sequence of streaking.

As illustrated in FIG. 11, the first spreader head controlled by spreader assembly 119 will spread inoculum 14 through a segment 162. The second segment 163 controlled by spreader assembly 120 will also subtend an angle of about 110° but will overlap segment 162 by about 35°. The overlapping area is indicated at 164. This then means that inoculum 14 which has been spread by the first head into area 164, will be diluted by being spread into segment 163 by the second head. Similarly, assembly 121 will streak segment 165 which also subtends an angle of 110° and has a portion 166 overlapping segment 163. The fourth head controlled by assembly 122 similarly provides a segment 167 of 110° having a portion 168 which overlaps segment 165. This then leaves a segment 169 which has not been streaked and which separates the portion of the Petri plate in which the inoculum was deposited from the portion where the inoculum has been streaked in successive dilutions.

Upon the completion of the streaking operation it is desired to replace the lids of the Petri plates and transfer them to an unload carousel 69 which is identical in design to the initial load carousel 17 illustrated in FIG. 4. This is accomplished by unload cylinder 75 which is actuated by unload pneumatic value 146 as operated by cam 124 shown in FIG. 12. Petri plate 10 is therefore moved by unloading cylinder 75 up into engagement with lid 11 and then the unload cylinder pushes the assembled Petri plate and lid up into carousel 69 where stack support 20 is biased to permit the assembled Petri plate to be loaded into the carousel, and then returns under the influence of spring 22 to retain the Petri plate in the unload carousel. Once the loading of the Petri plate into the carousel is accomplished the unload cylinder 75 retracts. Upon completion of sterilization the cycle control cam 126 in FIG. 12 shuts off the drive motor until and unless reactivated due to the presence of an oriented plate to be processed.

As a consequence, the inoculum of unknown concentration has now been sequentially diluted over the medium surface in a mechanical fashion which is independent of human judgment. The plates are now incubated at a suitable temperature such as 35° C. and read the next day to identify the microorganism.

Figure 13:
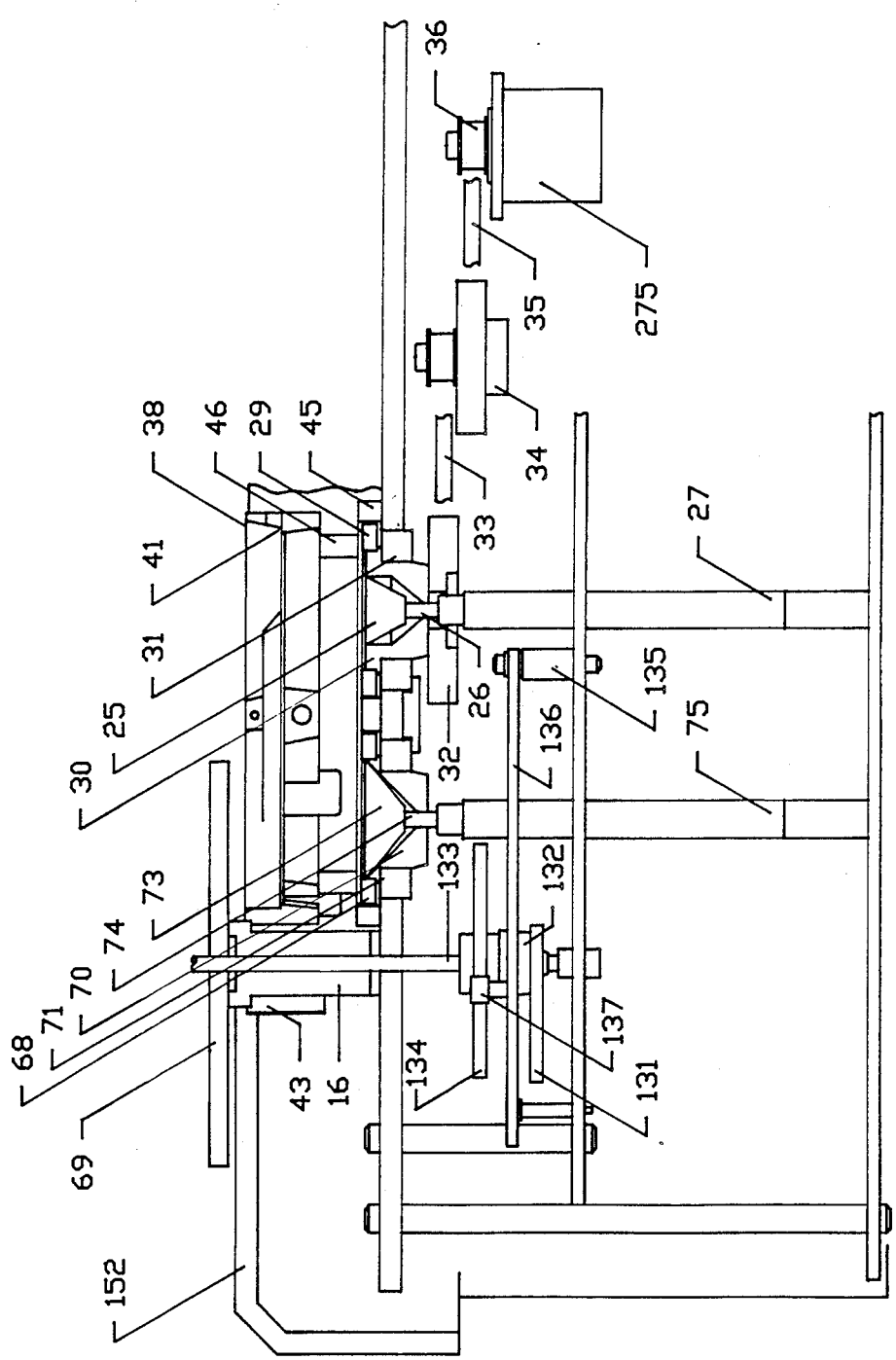
FIG. 13 is a section on the line 13—13 of FIG. 2.

FIGS. 12 and 13 show orientation motor 275 which drives a pulley 32 of orientation station 29 through reduction pulley assembly 34. As shown in detail in section view 13, pulley 32 is attached to orientation pivot 30 which is mounted in orientation bearing 31. Plate holder 29 is attached to orientation pivot 30. A rod 26 forming part of load cylinder 27 is guided by orientation pivot 30 and has mounted on it load piston 25.

Figure 5:
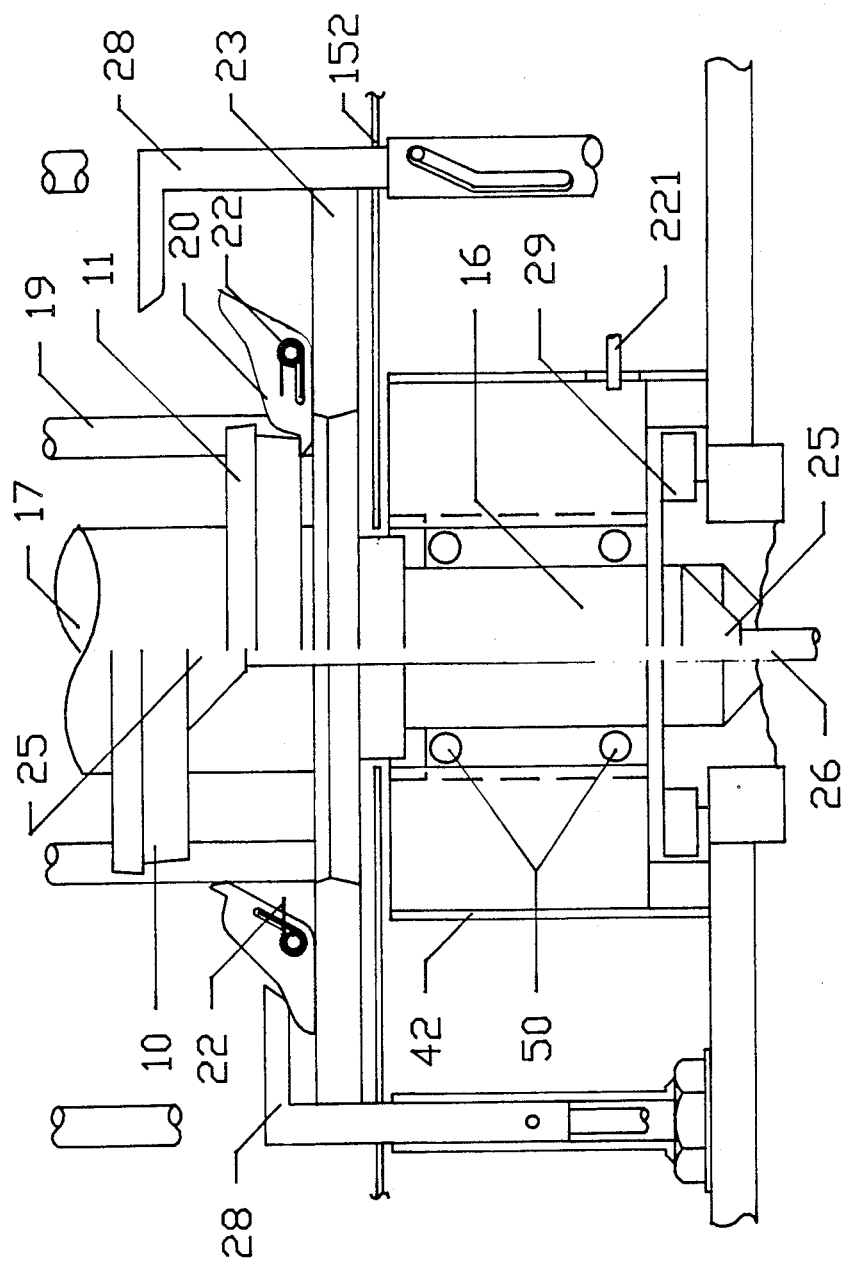
FIG. 5 is a detailed section view of a Petri plate retainer.

As explained in connection with the description of FIG. 5, when load cylinder 27 reaches the bottom of its stroke an orientation switch 226 energizes the orientation motor 275 for a timed interval. If no plate is sensed by sensor 221 the orientation motor stops after completion of the cycle of processing the previous plate. If a plate is sensed, rotation continues until orientation mark 15 is sensed at which time orientation motor 275 stops. The plate that has been sensed will be ready for transfer after completion of the spreading cycle. If there is no orientation mark but there is a plate, provision is made by a timer for an audible and visible signal to alert the operator.

Drive motor 277 is started by switch 235 as previously described. It drives oscillator crank 76 through belt 78. Oscillator crank 76 is joined to oscillator arm 72 through connecting rod 77 which is attached to oscillator pivot 70 which is mounted in oscillator bearing 71 onto which is mounted oscillator plate holder 68. Unload cylinder 75 which includes rod 74 is guided by oscillator pivot 76 and has attached to it unload piston 73.

Drive motor 277 is also connected by belt 81 to reduction idler pulley assembly 82 which in turn drives cam shafts 83 and 84 through belts 85 and 86. Cam shafts 83 and 84 in turn drive cam shafts 87 and 88 through belts 89 and 90.

Sterilization cam 125 is mounted on cam shaft 83. It activates sterilization switches 283, 285, 284 and 286 sequentially which in turn energize contacts 116 and 117 at the four head locations.

Sterilization verification cam 127 is mounted on cam shaft 88. It actuates switches 218 and 262 simultaneously. Switch 262 is normally closed and conducts the sterilization current. Then during the dwell of the sterilization cycle, switch 262 interrupts the sterilization circuit. If the circuit is working properly the continuity is maintained by relay contacts held closed by switch 218. If there is a malfunction the relay is not energized and the system shuts down with an audible and visual warning signal.

Unload cam 224 mounted on cam shaft 87 actuates four way pneumatic valve 146 which controls unload cylinder 75, raising it to lift a Petri plate on plate holder 68 into its lid and on upwards into the unload carousel 69 and then retracts the cylinder to its lower position.

Cycle cam 126 mounted on cam shaft 84 activates switches 230 and 276. Switch 276 upon actuation by cam 126 shuts down drive motor 277. Switch 230 actuated by cam 126 signals cycle completion.

If plate sensor 221 locates no plate it activates carousel rotation cylinders 129 which extend to rotate carousel actuator arm 131 which acting through one way clutch 132 rotate carousel shaft 133 through 90°. Index cam 134 is attached to shaft 133 and is indexed by index assembly 135. Carousel rotation cylinder 129 actuates limit switch 243, 247, 255 and 256 at the end of its stroke. Spring 138 maintains tension of index arm assembly 135 against index cam 134. Limit switches 243 & 247 on the load carousel rotation and unload carousel rotation act in series to de-energize rotation cylinders 129 returning them to their retracted position. Switch 255 and 256 restarts the machine cycle to process another stack of Petri plates.

Figure 14:
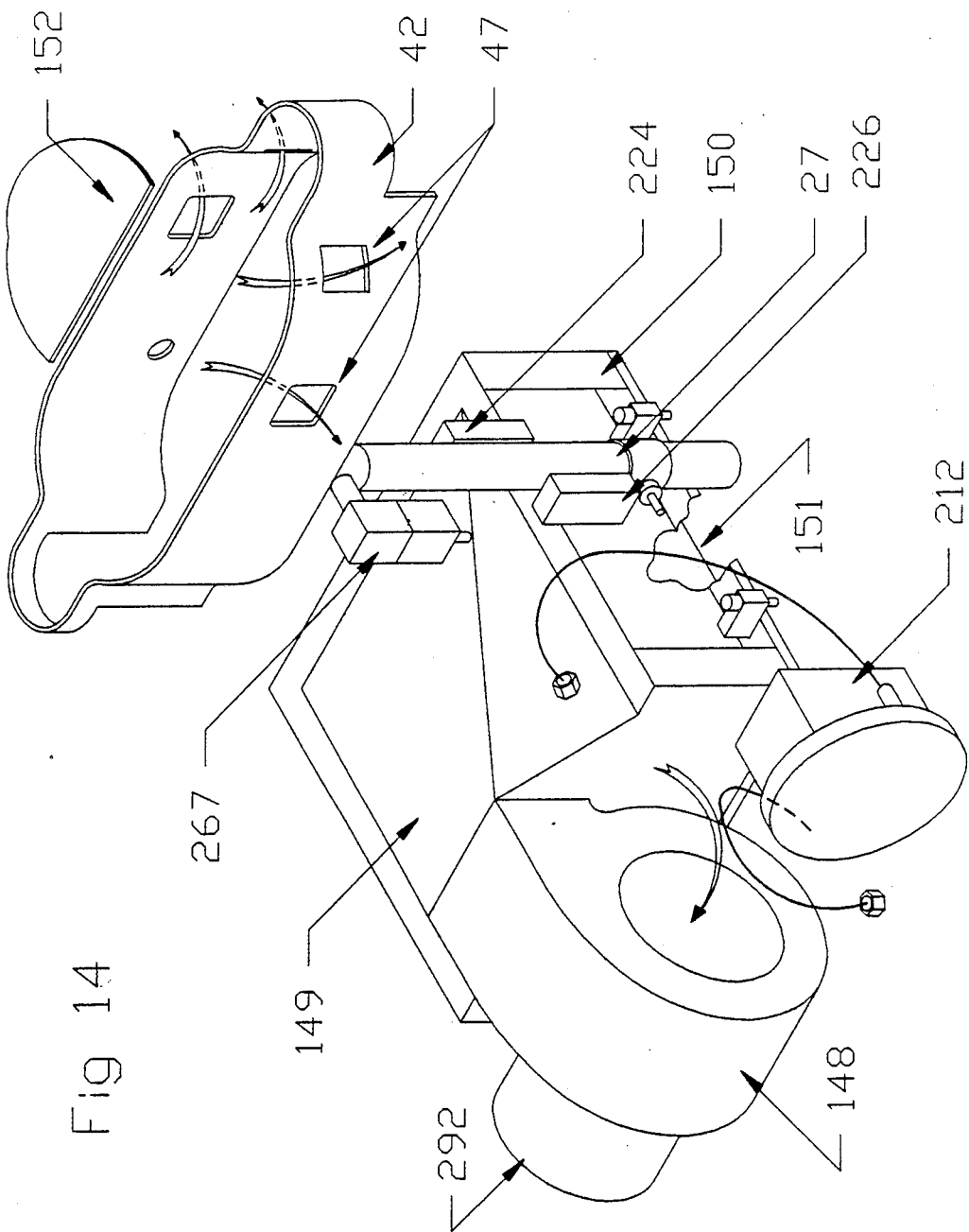
FIG. 14 is an isometric view of a negative pressure filter system.

FIG. 14 is an isometric view of a negative pressure filter system which can be used in association with the apparatus described in the other drawings for the purposes of protecting laboratory personnel and the environment from biohazardous aerosols and contaminents. If these should be released during processing of the Petri plates the system shown in FIG. 14 will cause the biohazardous materials to be directed through a purifying filter. The internal environment of the apparatus is maintained under a negative pressure to the laboratory environment so that air flow is in through the top openings 47 of the apparatus, through fan assembly 148 into diffuser assembly 149 and through HEPA filter 150 and is exhausted through opening 151 in the bottom of the machine. This safety feature is monitored through differential sensor 212 which assures that the interim pressure is negative to the exterior of the apparatus. Secondarily the inward air flow through openings 47 (shown in FIG. 6) cools copper bars 110 and 111 and element 113 resulting in faster element cooling following sterilization. It is preferred that a housing (partially shown at 152) enclose the apparatus to direct and confine the air flow so that the air flow goes past the Petri plates to direct any biohazardous material to the filter 150.

Figure 15:
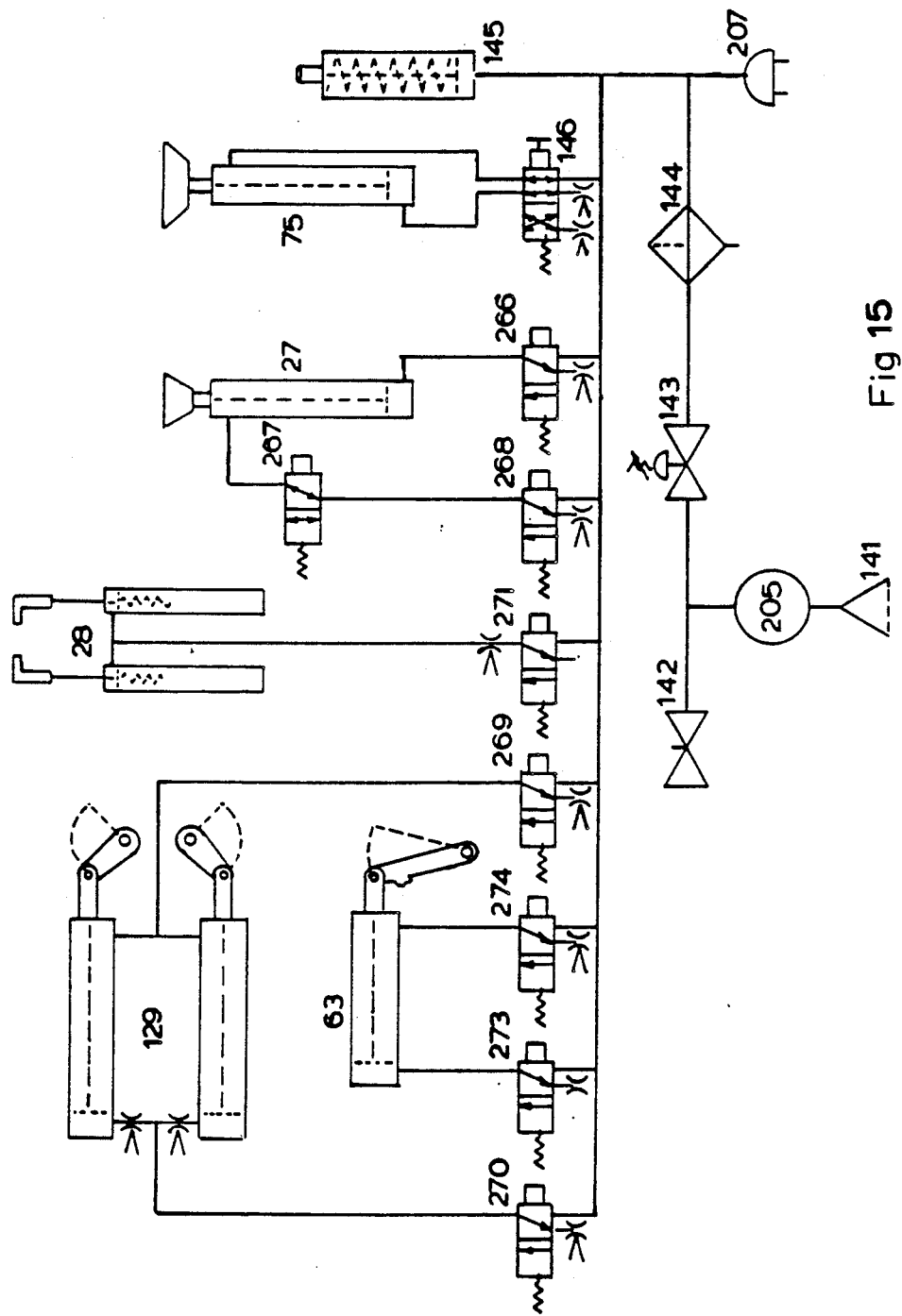
FIG. 15 is a schematic diagram of the pneumatic controls.

The pneumatic system illustrated in FIG. 15 consists of an electrically powered compressor 205 provided with a pre-filter 141 and relief valve 142. The output passes through regulator 143 and filter separator 144 to accumulator 145 and to seven solenoid valves 266, 268, 269, 270 271, 273, 274 and one mechanically activated valve 146 and the pressure switch 207. Valve 146 is a four-way valve actuated by the cam 124 on shaft 87 and controls the unload cylinder 75. Flow controls on the exhausts from valve 146 allow speed control adjustment. The load cylinder 27 is controlled by three solenoid valves 266–267 and 268. Up stroke pressure is provided by valve 266 and down stroke by 268. 267 is used to restrict up stroke travel during "in cycle" operation.

Valve 271 provide air pressure to the stack support actuating cylinders 28 through a flow control.

Valves 273 and 274 control movement of the transfer cylinder 63 again, speed control being achieved through flow controls on exhausts. Valves 269 and 270 control air flow to the carousel rotation cylinders 129, valve 270 providing the air pressure to rotate the carousel shafts 133 through individual speed controls to the two carousel rotation cylinders 129. Valve 269 provides pressure to retract cylinders 129.

Figure 16:
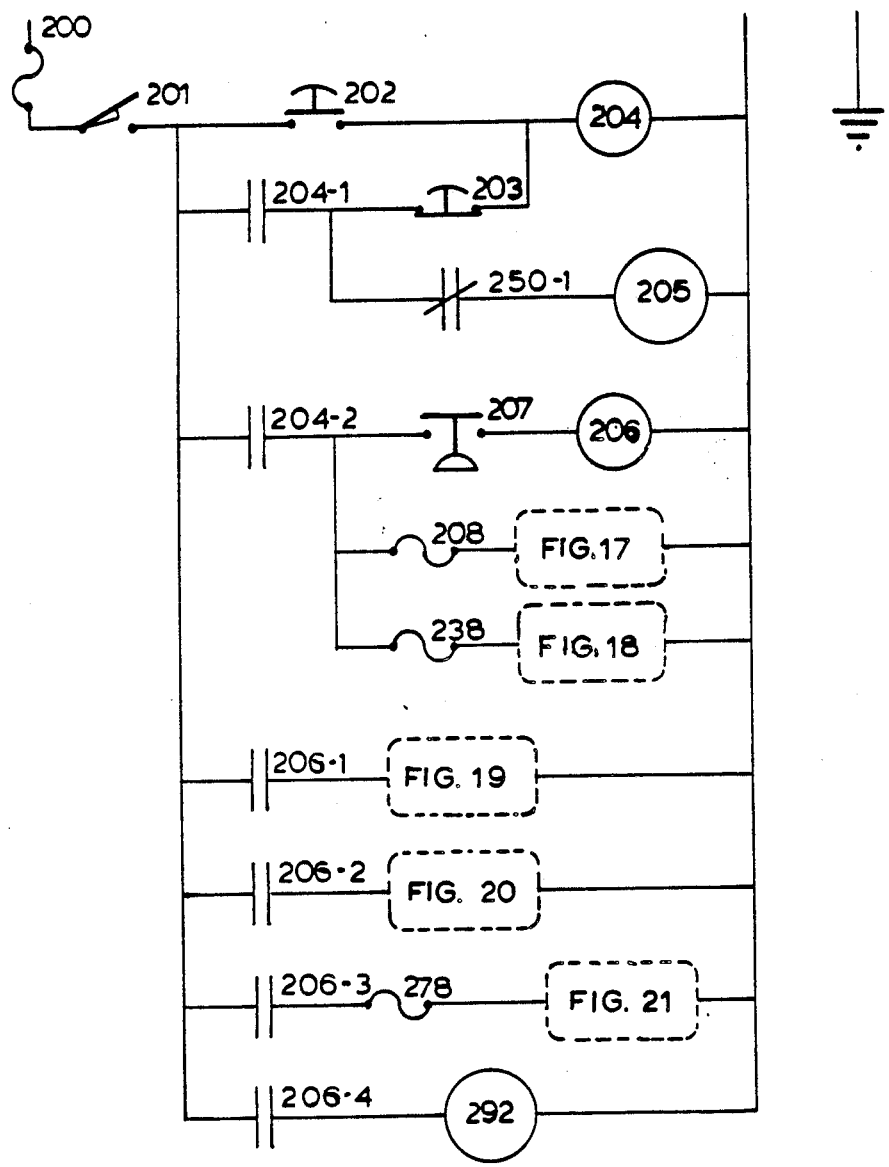
FIGS. 16, 17, 18, 19, 20 and 21 are diagrams showing the electrical controls.

The electrical system requires a 110/120 V alternating current power supply with a ground. As indicated on FIG. 16, incoming power supply is protected by 4 amp. fuse 200. Master switch 201 is a maintained contact on/off switch. Momentary contact power push button 202 energizes relay coil 204, which locks up through contacts 204–1, and "stop" push button 203, which is normally closed. Contacts 204–1 also power compressor 205 through normally closed contacts 250–1 of relay 250. Contacts 204–2 power pressure switch 207, fuses of 208 and 209 and the circuits of FIGS. 17 and 18. The closing of pressure switch 207 as air pressure is built up by compressor 205 energizes the coil of relay 206. Contacts 206-1 energize the circuits described in FIG. 19. Contacts 206-2 energize the circuits described in FIG. 20. Contacts 206—3 power fuse 278 and the circuits of FIG. 21. Contacts 206-4 power fan motor 292.

Figure 17:
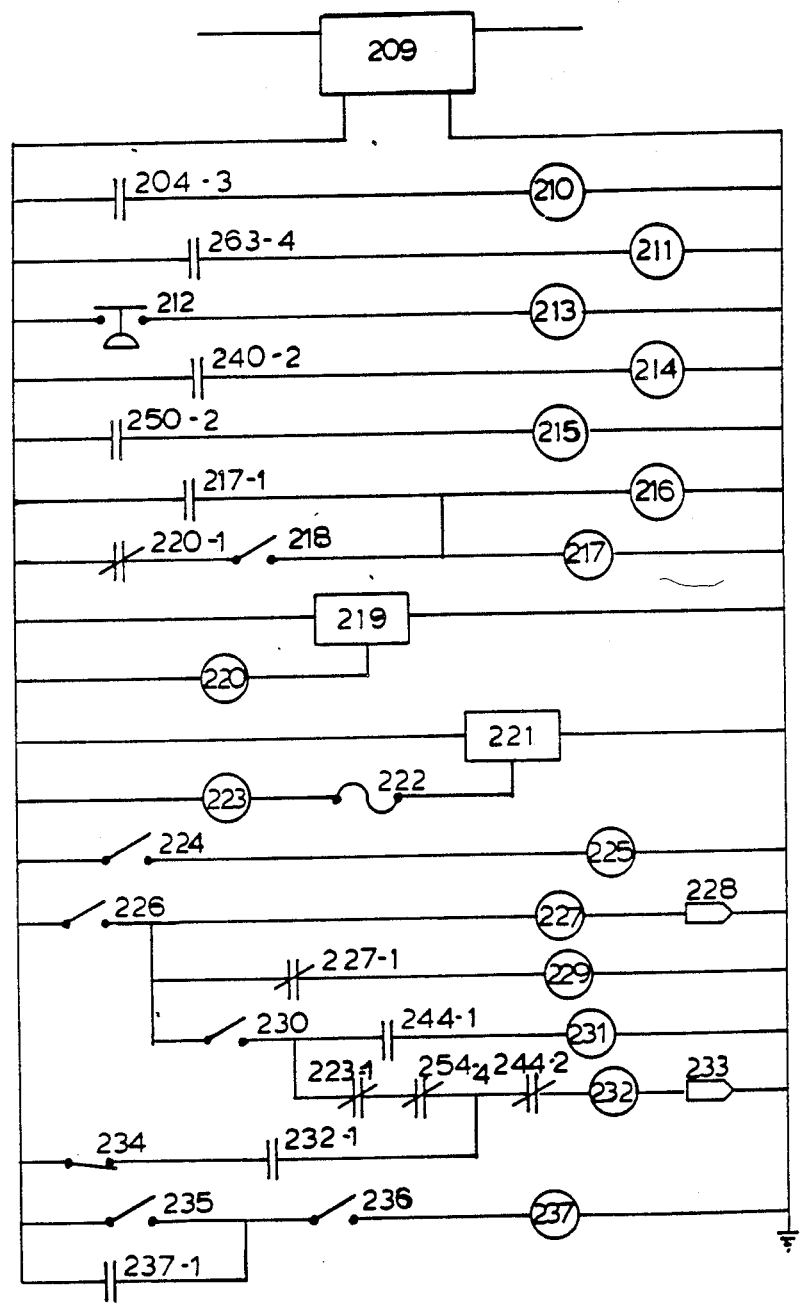

Power from 1 amp. fuse 208 (in FIG. 16) provides the primary 12 volt DC power supply 209 as shown in FIG. 17. Contacts 204–3 which are closed by relay coil 204 (in FIG. 16) supplies power to indicator light 210 informing the operator that the system is powered. Closing of contacts 263–4 and lighting of light 211 indicates that machine is in cycle.

Closing of pressure switch 213, and thereby the lighting of light 213 indicates an excessive pressure drop across the filter 150 and prompts filter replacement. Closing of contacts 240–2 lights 214 indicating that the optic sensing system 221 has sensed a plate but cannot find a mark and prompts the operator to unload the plate and mark the innoculum location.

Closing of contacts 250–2 lights light 215 indicating that no plate has been sensed and that the machine has completed its available work and should be reloaded or shut down.

Lighting of light 216 indicates the closing of sensor switch 218 without the opening of contacts 220–1 confirming that the current sensor 219 did not sense sterilization current and indicating a sterilization failure. Contacts 217–1 lock up the circuit maintaining the alert signal and preventing further operation of the machine without correcting the sterilization fault.

Optic sensor 221 controls relay coil 223 and is protected by 1/10 amp. fuse 222. Hall effect switch 224 on the load cylinder 26 closes when the load piston rises to contact with the plate stack resting on transfer arms 50 when the machine is in cycle.

Hall effect switch 226 on load cylinder 26 closes when the load piston is in its down position. It immediately powers relay coil 229, which is interrupted after the time interval set by timer 228 energizing relay coil 227 and opening contacts 227–1. Closing of cycle switch 230 indicating completion of a cycle energizes coil 232 after a time delay established by timer 233, unless prevented by opening of contacts 223–1, 259–1 or 249–2. Closing of contacts 249–1 energizes relay coil 231. Contacts 232–1 locks up relay coil 232 once energized unless dropped off by opening of contacts 244–2, or the opening of limit switch 234 by the forward movement of the transfer carriage 48 on which is mounted striker 52.

Switch 235 is provided by the normally open contacts of the same switch as 234. Closing of this switch along with switch 236, also on the switch assembly 64, energizes relay coil 237 which then locks up through contacts 237–1. Switch 235 can reopen without dropping relay coil 237 which is however dropped on the opening of switch 236.

Figure 18:
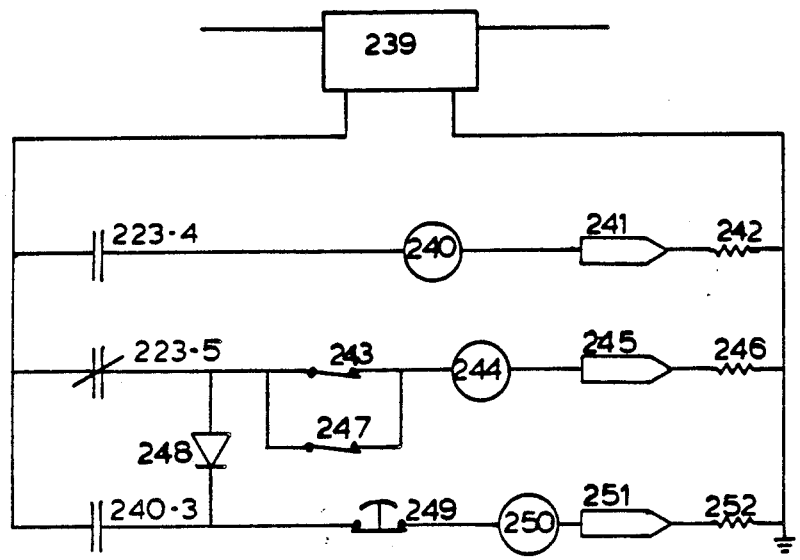

In FIG. 18 power through 1 amp. fuse 238 provides the primary supply to 24 volt DC power supply 239. Contacts 223–4 close on plate sensing by sensor 221 and start timing by striking timer 241 to energize relay coil 240 through voltage dropping resister 242, is a mark 15 is not found. If a plate is not sensed contacts 223–5 remain closed and with rotation cylinders 129 activated and switches 243 and 247 closed, striking timer 245 starts timing the energizing of relay coil 244 through voltage dropping resistor 246. Either closing of contacts 240–3 or through diode 248 and normally closed contacts of cycle push button 249 initaes timing of striking timer 251 to energize relay coil 250 through voltage dropping resistor 252.

Figure 19:
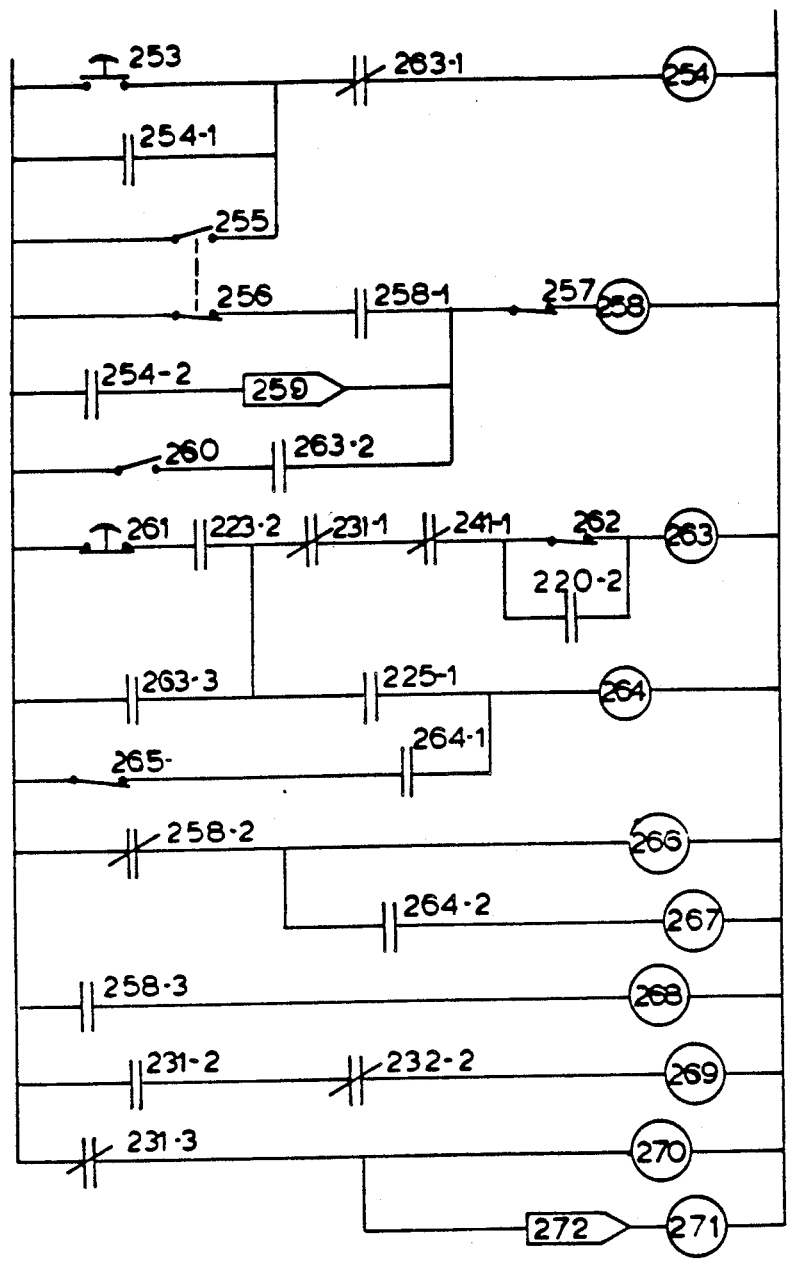

FIG. 19 covers circuitry powered through contacts 206-1. Cycle push button 253 energizes relay coil 254 through closed contacts 263-1 and locks up through 259-1 or alternately through closing of switch 255 activated by the carousel rotation cylinder 129 to restart the cycle upon carousel change.

Normally closed contacts 256 of the same switch interrupt the lock up circuit to rely coil 258 which can also be interrupted by switch 257 which is activated by the striker 52 on the carriage 48 on the forward stroke after the plate 10 and cover 11 being transferred have cleared the load piston 25. Closing of contacts 254-2 starts timing cycle of delay 259 which powers relay coil 258 on first cycle switch 260 which closes on the transfer slide being fully retracted and contacts 263-2 energize relay coil 258 during normal operation.

Cycle switch contacts 261 (normally closed) allow contacts 223-2 to energize relay coil 263 and lock up through contacts 263-3 until dropped off by contacts 231-1, contacts 241-1, or in the absence of power to close contacts 220-2 from the current sensor verification switch 262.

With contacts 263-3 or 223-2 closed, closing of contacts 225-1 powers relay coil 264 which will lock up through switch 265 which is closed in the retracted position of the striker 52 on carriage 48. Normally closed contacts 258-2 energize solenoid valve 266 which provide air pressure to extend the load cylinder 27.

The closing of contacts 264-2 energizes solenoid valve 267 inhibiting the extension of the load cylinder 27. Closing of contacts 258-3 energizes solenoid valve 268 to lower the load piston 25. Closing of contacts 231-2 powers solenoid valve 269 through normally closed (N.C.) contacts 232-2 entending carousel rotation cylinders 129. N.C. contacts 231-3 energize solenoid valve 270 providing air pressure to retract carousel rotation cylinders 129 and also energizes timer 272 to start timing to power solenoid valve 271 which allows air pressure to activation cylinder 28.

Figure 20:
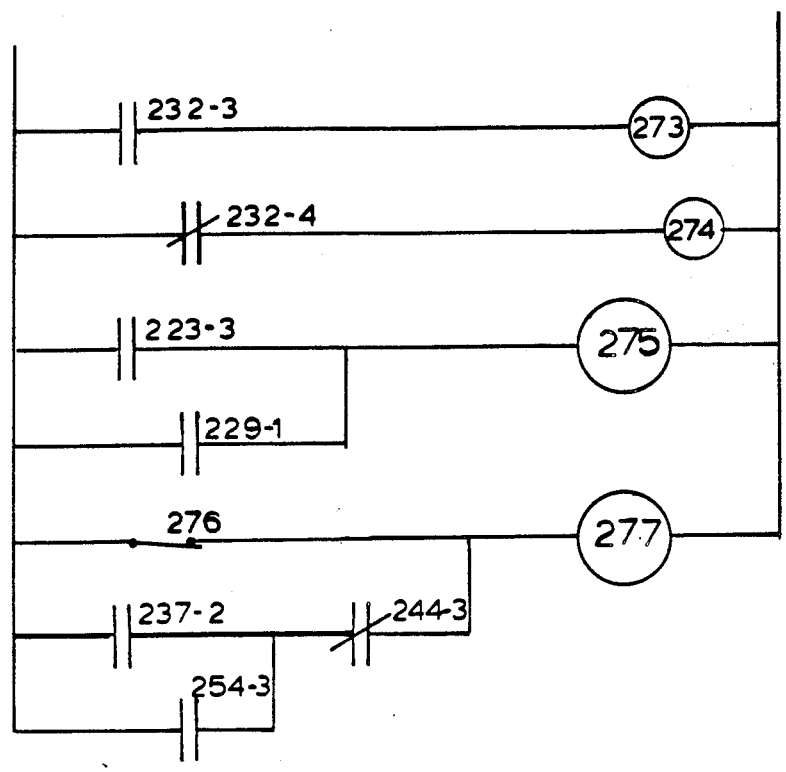

The circuit shown in FIG. 20 is powered through contacts 206-2. Contacts 232-3 on closing energize solenoid valve 273 moving transfer slide 48 to move plate 10 and lid 11 from orientation station 29 to streaking station 68.

Contacts 232-4 return transfer slide 48 to retracted position. Closing contacts 223-3 or 229-1 will start orientation motor 275. Cycle switch contacts 276 maintain power to cycle motor 277 once started from the stop or open position of switch 276 by the cycle switch 253 actuated contacts 254-3 on the first cycle, or by the combined activations of switches 235 and 236 by movement of the transfer slide 48 on subsequent cycles.

Figure 21:
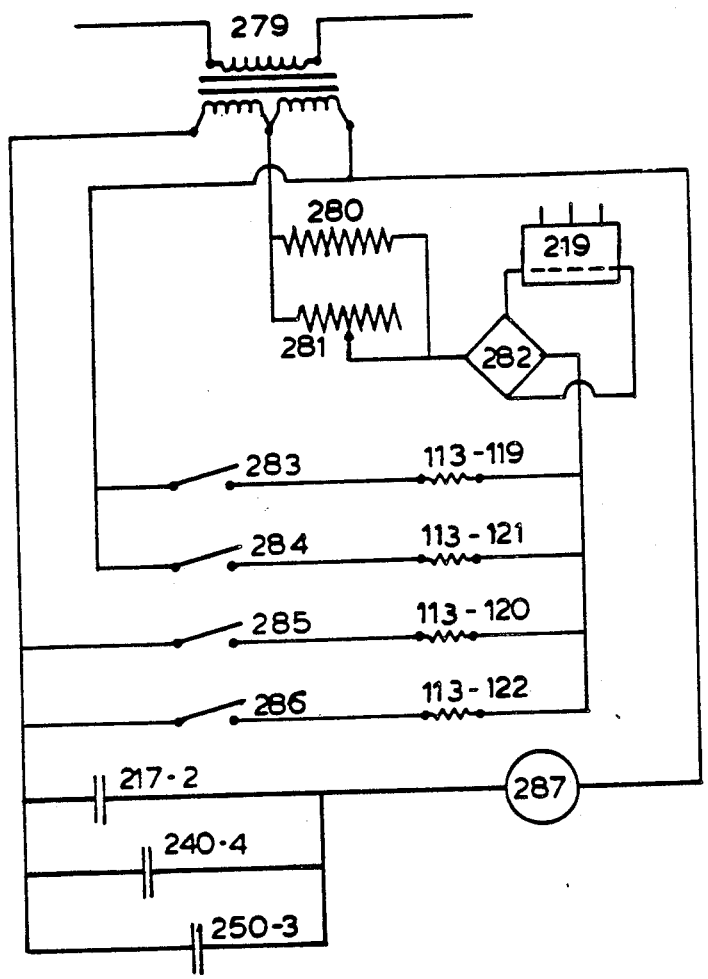

The circuit shown in FIG. 21 is powered through 2 amp. fuse 278 which energizes the primary coil of transformer 279 to provide 14 volt AC output with a center tap to provide 7 volt. The center tap is taken through a fixed resistor 280 and variable resistor 281 to allow sterilization voltage adjustment to rectifier 282. A positive-negative loop from rectifier 282 is taken through current sensor 219 and the AC line from the rectifier 282 continues to form the connection for element 113 sterilization circuits. Sterilization switch 283 on closing allows current to flow through element 113 at head position 119.

Similarly switch 285 next in sequence through feed from opposite winding of the transformer allows current to flow through element 113 (shown in FIG. 8) at position 120 (in FIG. 11). Switch 284 causes current flow to heat element 113 at position 121 and switch 286 causes current flow to heat element 113 at position 122. Two elements are, therefore, not on the same transformer winding at the same time as the other two, though there is overlap on the cam timing. Contacts 217-2, 240-2 and 250-3 signal loop failure in the absence of an orientation mark and no further plate availability, respectively. These provide an audible alert signal by energizing buzzer 287. Timer 251 on timing out drops off the compressor 205 which allows pressure switch 207 to open, dropping relay coil 206. This de-energizes all 206 circuits.

The D.C. circuits are maintained and the fault signal maintained until the machine is shut off using stop switch 203.

We claim:

1. Apparatus for streaking a sample on a Petri plate having a layer of culture medium inoculated with a sample comprising:
   means for bringing a sequential plurality of spreading arms, each having a spreading head, in contact with the surface of a culture medium;
   means for moving each said spreading head in a sinuous path across the culture medium to streak an inoculated sample in a first segment of a plate at a given dilution;
   means for angularly displacing the sinuous paths of the second and any subsequent spreading heads from the sinuous path of the preceding spreading head so that a second segment of the plate in which the second and subsequent spreading heads streak the sample will partially overlap the respective preceding segment, to cause said inoculated sample to be streaked in said second segment at a dilution greater than said given dilution.

2. Apparatus as claimed in claim 1, comprising a support for the Petri plate, said support being movable about a substantially vertical axis, means for angularly moving said support about its vertical axis, means for bringing a first one of said spreading heads in contact with the surface of the culture medium and moving said spreading head in relation to the surface of the culture medium in a sinuous path to streak the inoculated sample in said first segment of the culture medium and moving said second spreading head in relation to the surface of the culture medium in a sinuous path to streak the inoculated sample in said second segment of the culture medium angularly displaced from but overlapping the first segment.

3. Apparatus as claimed in claim 1, in which the means for moving the spreading heads comprises means for sweeping a first one of said spreading heads back and forth across the surface of the culture medium in said first segment of the plate and means for contacting said second spreading head with the culture medium and means for sweeping said second head back and forth across the surface of the culture medium in said second segment of the plate angularly displaced from but overlapping the first segment of the plate.

4. Apparatus as in claim 2 comprising means for oscillating said support about a substantially vertical axis through a given angle, means for bringing a first one of said spreading heads in contact with the surface of the culture medium and moving it radially from close to the periphery of the Petri plate towards the centre of the Petri plate while the Petri plate is subjected to a plurality of oscillations to streak the inoculated sample in a first segment of the culture medium, means for sequentially bringing said second spreading heads into contact with the surface of said culture medium and moving it radially along a line angularly displaced from the line of movement of said first spreading head by an angle less than the given angle while the Petri plate is subjected to a plurality of oscillations, so that the second of said spreading heads would streak the inoculated sample in a second segment of the culture medium overlapping said first segment.

5. Apparatus as claimed in claim 4 comprising means for sequentially bringing a third of said spreading heads into contact with the surface of a culture medium and moving it radially along a line angularly displaced in the direction of displacement of the second spreading head from the line of movement of the second spreading head by an angle less than the given angle while the Petri plate is subjected to a plurality of oscillation cycles so that the third of said spreading heads would streak the inoculated sample in a third segment of the culture medium overlapping said second segment but not said first segment, to cause said inoculated sample to be streaked in the first, second the third segments at successively greater dilutions.

6. Apparatus as claimed in claim 5 comprising means for sequentially bringing a fourth of said spreading heads in contact with the surface of said culture medium and moving it radially along a line angularly displaced in the direction of displacement of said second and third spreading heads from the line of movement of said third spreading head by an angle less than the given angle while the plate is subjected to a plurality of oscillations so that the fourth of said spreading heads would streak the inoculated sample in a fourth segment of the culture medium overlapping said third segment but not overlapping the first or second segments, to cause said inoculated sample to be spread in the first, second, third and fourth segments at successively greater dilutions.

7. Apparatus as in claim 4, in which the given angle of oscillation is about 110°.

8. Apparatus as in claim 4, in which the overlap between sequential segments is about 35°.

9. Apparatus as in claim 1, in which each of said spreading heads comprises a wire and comprising means for automatically heating said wire element to sterilize it when said element is not in contact with the culture medium.

10. Apparatus as in claim 4, in which the spreading heads are carried by spreader arms extending in directions radial to said support for a Petri plate and in which a cam actuates each of said spreader arms to advance or retract it in a radial direction and another cam actuates each of said spreader arms to raise or lower the spreader head to lower the spreader head onto the culture medium and remove it therefrom.

11. Apparatus as in claim 1, comprising means for stacking a number of Petri plates, means for moving successive Petri plates to an orientation position where each Petri plate will be oriented by rotating the Petri plate to align a place where the Petri plate was inoculated in a predetermined position and means for moving the Petri plate from the orientation position to a work position where said spreading heads are successively lowered onto and moved across the culture medium.

12. Apparatus as in claim 1, comprising means for stacking a number of Petri plates having covers, means for moving successive Petri plates to an orientation position where each Petri plate will be oriented by rotating the Petri plate to align the place where the Petri plate was inoculated in a predetermined position, means for separating the covers from each Petri plate, and means for moving the Petri plates and associated but separated covers from the orientation position where spreading heads are successively lowered out in and moved across the culture medium and then withdrawn, and means for replacing the covers on their respective Petri plates.

13. Apparatus as in claim 1, comprising first and second carousel means for stacking a number of Petri plates including covers, the first carousel being to accommodate Petri plates and the second carousel being to accommodate Petri plates that have been streaked; means for successively loading Petri plates from the first carousel to an orientation position means for lifting the covers from the Petri plates, means for moving the Petri plates with associated covers above them to a work station where spreading heads are successively lowered onto and moved across the culture medium and then withdrawn, means for replacing the covers and means for successively loading the Petri plates into the second carousel, and means for indexing the carousel means.

14. Apparatus as in claim 1, comprising first and second removable carousel means for stacking a number of Petri plates including covers, the first carousel being to accommodate Petri plates and the second carousel being to accommodate Petri plates that have been streaked; means for successively loading Petri plates from the first carousel to an orientation position means for lifting the covers from the Petri plates, means for moving the Petri plates with associated covers above them to a work station where spreading heads are successively lowered onto and moved across the culture medium and then withdrawn, means for replacing the covers and means for successively loading the Petri plates into the second carousel, and means for indexing the carousel means.

15. Apparatus as in claim 1 comprising first and second carousel means for stacking a number of Petri plates including covers, the first carousel means for stacking being to accommodate Petri plates and the second carousel means for stacking being to accommodate Petri plates that have been streaked; means for successively down loading Petri plates from the first carousel means to an orientation position, means for lifting the covers from the Petri plates, means for moving the Petri plates with associated covers above them to a work station where spreading heads are successively moved in contact with and across the surface of the culture medium and then withdrawn, means for replacing the covers and means for successively uploading the Petri plates into the second carousel means for stacking, said means for moving the Petri plates with associated covers above them to a work station comprising guides for the Petri plates and covers and a transfer carriage with pusher arms engaging the Petri plates and covers and means for indexing the carousel means.

16. Apparatus as in claim 1 comprising means for stacking a number of Petri plates, means for moving successive Petri plates to an orientation position where each Petri plate will be oriented by rotating the Petri plate to align the place where the Petri plates was inoculated in a predetermined position and means for moving the Petri plate from the orientation position to a work position where spreading heads are successively brought in contact with and moved across the surface of the culture medium in a predetermined pattern to streak the sample.

17. Apparatus as in claim 1 comprising means for stacking a number of Petri plates having covers, means for moving successive Petri plates to an orientation position where each Petri plate will be oriented by rotating the Petri plate to align the place where the Petri plate was inoculated in a predetermined position, means for lifting the covers from each Petri plate, and means for moving the Petri plates and associated but separate covers from the orientation position where spreading heads are successively brought in contact with and moved across the surface of the culture medium in a predetermined pattern to streak the sample and then withdrawn and means for replacing the covers on their respective Petri plates.

18. Apparatus as in claim 1 comprising first and second means for stacking a number of Petri plates including covers, the first means for stacking being to accommodate Petri plates and the second means for stacking being to accommodate Petri plates that have been streaked; means for successively loading Petri plates from the first stack to an orientation position, means for separating the covers from the Petri plates, means for moving the Petri plates with a associated covers above them to a work station where spreading heads are successively brought in contact with and moved across the surface of the culture medium in a predetermined pattern to streak the sample and then withdrawn, means for replacing the covers and means for successively loading the Petri plates into the second means for stacking.

19. Apparatus as in claim 1 comprising first and second means for stacking a number of Petri plates including covers, the first means for stacking being to accommodate Petri plates and the second means for stacking being to accommodate Petri plates that have been streaked; means for successively down loading Petri plates from the first stack to an orientation position, means for separating the covers from the Petri plates, means comprising guides for the Petri plates and covers and a transfer carriage with pusher arms engaging the Petri plates and covers, for moving the Petri plates with associated covers above them to a work station where spreading heads are successively brought in contact with and moved across the surface of the culture medium in a predetermined pattern and then withdrawn, means for replacing the covers and means for successively loading the Petri plates into the second means for stacking.

20. Apparatus as in claim 1, means for bringing said spreading head in contact with the culture medium and causing it to move relative to the culture medium to streak the inoculated sample, means for removing the spreading head from the culture medium to a position remote from the culture medium and means for sterilizing the spreading head while it is in the remote position.

21. An apparatus as in claim 20 in which the spreading head is heated to sterilize it.

22. An apparatus as in claim 21 in which the spreading head is a wire element.

23. An apparatus as in claim 21 in which the spreading head is supported by a spreader arm and in which the spreader arm is associated with electrical contacts which are closed when the spreader head is removed to the remote position to cause a current to pass through the wire element and sterilize it.

24. An apparatus as in claim 1, in which means are provided to create a negative pressure to draw air past the Petri plate being streaked and directing such air to purification means.

25. Apparatus for spreading samples inoculated in a culture medium over the surface of said culture media contained in Petri dishes, said apparatus including a support and comprising:
 (1) means for holding and transporting a plurality of Petri dishes to and from said support of said apparatus;
 (2) said support including an orientation station and means for sequentially loading and unloading a Petri dish into said orientation station;
 (3) means adjacent said orientation station for removing and replacing the lid for the Petri dish in said station;
 (4) means for identifying and locating the site where said sample was inoculated onto said culture media;
 (5) means for orienting said Petri dish to being said site into a preselected position;
 (6) means for transferring said Petri dish and its separate lid from said orientation station to a spreading station on said support;
 (7) means for oscillating said Petri dish at said spreading station; said spreading station including four spreading arms angularly displaced about said spreading station, each said spreading arm having a spreading head;
 (8) means for sequentially bringing said angularly displaced spreading heads into contact with the surface of said culture media;
 (9) means for sequentially moving said spreading heads radially across the surface of said culture media while it is being oscillated so that the resulting sinuous paths of subsequent spreading heads overlap the path of the preceding head;
 (10) said means for sequentially moving including means for retracting and sterilizing said spreading heads between successive Petri dishes.

26. Apparatus as claimed in claim 25, wherein said means for holding and transporting the Petri dish comprises two portable carousels, one of which is a load carousel to accommodate a Petri plate ready for orienting and then spreading and the other of which is an unload carousel to accommodate a Petri plate that has been spread; means for holding up to four stacks of Petri dishes including means for each stack to hold a plurality of Petri dishes; means for hand loading Petri dishes from the top; means for removing Petri dishes from the bottom; means for loading Petri dishes from the bottom; means for locating and securing a carousel on said support of said apparatus; means for sequentially orienting the four stacks of the load carousel over the orientation station and the four stacks of the unload carousel over the spreading station.

* * * * *